(12) United States Patent
Ouni et al.

(10) Patent No.: US 9,969,940 B2
(45) Date of Patent: *May 15, 2018

(54) USE OF RENEWABLE OIL IN HYDROTREATMENT PROCESS

(71) Applicant: Neste Oyj, Espoo (FI)

(72) Inventors: Tuomas Ouni, Helsinki (FI); Vainö Sippola, Espoo (FI); Petri Lindqvist, Porvoo (FI)

(73) Assignee: NESTE OYJ, Espoo (FI)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/932,566

(22) Filed: Nov. 4, 2015

(65) Prior Publication Data

US 2016/0060540 A1 Mar. 3, 2016

Related U.S. Application Data

(63) Continuation of application No. 14/273,024, filed on May 8, 2014, now Pat. No. 9,206,092, which is a (Continued)

(30) Foreign Application Priority Data

Feb. 15, 2011 (EP) .................................. 11154437

(51) Int. Cl.
*C07C 1/207* (2006.01)
*C07C 5/27* (2006.01)
(Continued)

(52) U.S. Cl.
CPC ............... *C10G 3/50* (2013.01); *A23D 9/007* (2013.01); *C07C 1/207* (2013.01); *C07C 5/27* (2013.01);
(Continued)

(58) Field of Classification Search
None
See application file for complete search history.

(56) References Cited

U.S. PATENT DOCUMENTS

| 4,512,878 A | 4/1985 | Reid et al. |
| 4,992,605 A | 2/1991 | Craig et al. |

(Continued)

FOREIGN PATENT DOCUMENTS

| CZ | 283 575 | 2/1998 |
| EP | 0 507 2017 A1 | 10/1992 |

(Continued)

OTHER PUBLICATIONS

Abhari et al., "New Routes Ethylene" EEPC Seminar in Berlin, Germany (2010).
(Continued)

*Primary Examiner* — Tam M Nguyen
(74) *Attorney, Agent, or Firm* — Finnegan, Henderson, Farabow, Garrett & Dunner, LLP (57) ABSTRACT

The use of bio oil from at least one renewable source in a hydrotreatment process, in which process hydrocarbons are formed from said glyceride oil in a catalytic reaction, and the iron content of said bio oil is less than 1 w-ppm calculated as elemental iron. A bio oil intermediate including bio oil from at least one renewable source and the iron content of said bio oil is less than 1 w-ppm calculated as elemental iron.

23 Claims, 3 Drawing Sheets

Related U.S. Application Data continuation of application No. 13/397,236, filed on Feb. 15, 2012, now Pat. No. 8,742,185.

(60) Provisional application No. 61/443,161, filed on Feb. 15, 2011.

(51) Int. Cl.

| | | |
|---|---|---|
| *C10G 3/00* | (2006.01) | |
| *A23D 9/007* | (2006.01) | |
| *C11C 3/12* | (2006.01) | |
| *C07C 69/604* | (2006.01) | |
| *C07C 69/66* | (2006.01) | |
| *C10G 45/58* | (2006.01) | |

(52) U.S. Cl.
CPC .......... *C07C 69/604* (2013.01); *C07C 69/66* (2013.01); *C10G 3/46* (2013.01); *C10G 45/58* (2013.01); *C11C 3/126* (2013.01); *C10G 2300/1014* (2013.01); *C10G 2300/1018* (2013.01); *C10G 2300/205* (2013.01); *C10G 2400/02* (2013.01); *C10G 2400/04* (2013.01); *C10G 2400/08* (2013.01); *C10G 2400/10* (2013.01); *C10G 2400/18* (2013.01); *C10G 2400/28* (2013.01); *Y02P 30/20* (2015.11)

(56) References Cited

U.S. PATENT DOCUMENTS

| | | |
|---|---|---|
| 5,079,208 A | 1/1992 | Lammers et al. |
| 5,298,639 A | 3/1994 | Toneboehn et al. |
| 6,203,695 B1 | 3/2001 | Harle et al. |
| 8,212,094 B2 | 7/2012 | Myllyoja et al. |
| 8,278,492 B2 | 10/2012 | Myllyoja et al. |
| 2003/0050492 A1 | 3/2003 | Copeland et al. |
| 2006/0293532 A1 | 12/2006 | Lee et al. |
| 2007/0010682 A1 | 1/2007 | Myllyoja et al. |
| 2008/0154073 A1 | 6/2008 | Petri et al. |
| 2009/0300970 A1 | 12/2009 | Perego et al. |
| 2010/0000908 A1 | 1/2010 | Markkanen et al. |
| 2010/0038284 A1 | 2/2010 | Vergel |
| 2010/0132251 A1 | 6/2010 | Sohling et al. |
| 2010/0240942 A1 | 9/2010 | Daudin et al. |
| 2011/0138680 A1* | 6/2011 | Dandeu .................. C11B 3/001 44/307 |

FOREIGN PATENT DOCUMENTS

| | | |
|---|---|---|
| EP | 1 396 531 A2 | 3/2004 |
| FR | 2 937647 A1 | 4/2010 |
| WO | WO 2007003709 A1 | 1/2007 |

OTHER PUBLICATIONS

Amended Petition dated Mar. 21, 2013 in Inter Partes Review No. IPR2013-00178.
Amended Petition dated Dec. 13, 2013 in Inter Partes Review No. IPR2014-00192.
Beare-Rogers, J., et al., "Lexicon of Lipid Nutrition" (IUPAC Technical Report), *Pure Appl. Chem.*, vol. 73, No. 4, pp. 685-744, 2001.
Bergerioux, C. et al., "Determination of Trace Element Pathways in a Petroleum Distillation Unit by Instrumental Neutron Activation Analysis," Journal of Radioanalytical Chemistry, vol. 54, No. 1-2, 1979, pp. 255-265.
Canola Laboratory Report, Summit Environmental Technologies, issued Feb. 27, 2013 (Ex. 1005 in IPR2013-00178).
Declaration of Edward L. Sughrue II dated Mar. 7, 2013 in Inter Parte Review No. IPR2013-00178.
Declaration of Edward Sughrue dated Nov. 21, 2013, Exhibit 1002 in *Syntroleum v. Neste* IPR2014-00192.
Declaration of James G. Goodwin, Jr., Ph.D. under 37 C.F.R. § 1.132, dated Nov. 13, 2012, cited in Reexamination Control No. 95/002,084.
Declaration of Nelson E. Lawson (with Tab A) dated Mar. 3, 2013 in Inter Parte Review No. IPR2013-00178.
Declaration of Pekka Aalto under 37 C F .R. § 1.132, dated Nov. 14, 2012, in Reexamination Control No. 95/002,084.
Deem, A.G. et al., "Catalytic Poisoning in Liquid-Phase Hydrogenation," Industrial and Engineering Chemistry vol. 33. No. 11, Nov. 1941, pp. 1373-1376.
Edgar, M.D. et al., "Analysis is key to hydrotreater troubleshooting," Oil & Gas Journal, vol. 82, Issue 23, Jun. 4, 1984. pp. 67-70.
Feng, Y. et al., "Chemical composition of tall-oil based cetane enhancer for diesei fuels." First Biomass Conference of the Americas: Energy, Environment, Agriculture, and Industry, vol. II, Aug. 30-Sep. 2, 1993, Burlington, Vermont, p. 863-875 (1993).
Galperin, L. B., "Hydroisomerization of N-decane in the presence of sulfur and nitrogen compounds." Applied Catalysis A: General 209 (2001) 257-268.
Garrido, M.D., et al., "Concentrations of metals in vegetable edible oils," Food Chemistry, vol. 50, 1994, DD. 237-243.
Gusmao, et al., "Utilization of Vegetable Oils as Alternative Source for Diesel-Type Fuel," Catalysis Today, 5:533-544 (1989).
Kubicka et al., "Ultraclean Fuels Obtained by Hydrodeoxydenation of Renewable Feedstocks: Deactivation of Deoxygenation Catalysts," Prep. Pap.-Am. Chem. Soc., Div. Fuel Chem., (2010), vol. 55, No. 1, p. 169-170.
MacDonald, "Fuel From Fats," ener G Alternative Sources Magazine (Sep./Oct. 2011).
Mag, T., "Canola Seed and Oil Processing," Canola Council of Canada, 1994.
Office Action issued in U.S. Appl. No. 11/415,707 dated Aug. 24, 2007.
Prakash: Dr. G. B., "A Critical Review of Biodiesel as a transportation fuel in Canada," GCSI—Global Change Strategies International Inc. (1998).
Przvbvlski, R., "Canola Oil: Physical and Chemical Properties," Canola Council of Canada; no date provided.
R. Antoniassi, et al., "Pretreatment of Corn Oil for Physical Refining," *JAOCS*, vol. 75, No. 10, 1998, pp. 1411-1415.
Search Report dated Jun. 1, 2011, by European Patent Office for Application No. 11154437.5.
Soveran, D.W. et al., "The Effect on Diesel Engine Emissions with High Cetane Additives from Biomass Oils," (1992).
Spataru, "is There a Future for Yellow Grease as a Fuel Additive?", Render 12-14 (Feb. 2001).
Stumborg, M., et al., "Hydroprocessed Vegebable Oils for Diesel Fuel Improvement," Liquid Fuels, Lubricants and Additives from Biomass, Proceedings of an Alternative Energy Conference (1994).
TOFA Laboratory Report. Summit Environmental Technologies, issued Feb. 27, 2013 (Ex. 1004 in IPR2013-00178).
Tyson, K. et al., "Biomass Oil Analysis: Research Needs and Recommendationss" Technical Report, National Renewable Energy Laboratory, Colorado (2004).
Wong, A. et. al., "Conversion of Vegetable Oils and Animal Fats into Paraffinic Cetane Enhancers for Diesel Fuels," Second Biomass Conference of the Americas (1995).
M. Swartz, *Method Validation*, in Handbook of Methods and Instrumentation in Separation Science, vol. 1 614-620 (Colin Poole ed., 2009), Waters Corporation, Milford, MA, USA.
IUPAC, Compendium of Chemical Terminology: Gold Book, 2nd ed., Compiled by A. D. McNaught and A. Wilkinson; Blackwell Scientific Publications, Oxford (1997). XML on-line corrected version: http://goldbook.iupac.org (2006-) created by M. Nic, J. Jirat, B. Kosata; updates compiled by A. Jenkins, doi:10.1351/goldbook.L03540.
European Committee for Standardization (CEN), EN 14241, Chimneys—Elastorneric seals and elastomeric sealants—Material requirements and test methods, 2013 (DIN, Berlin, Germany).
European Committee for Standardization (CEN), EN 12441-4, Zinc and zinc alloys—Chemical analysis, Part 4: Determination of iron (56) References Cited

OTHER PUBLICATIONS in zinc alloys—Spectrophotometric method, 2003 (DIN, Berlin, Germany).

* cited by examiner

USE OF RENEWABLE OIL IN HYDROTREATMENT PROCESS

CROSS-REFERENCE TO RELATED APPLICATIONS

This application claims the benefit of priority of U.S. patent application Ser. No. 14/273,024, filed May. 8, 2014, in turn, to U.S. patent application Ser. No. 13/397,236, filed Feb. 15, 2012, now U.S. Pat. No. 8,742,185 issued Jun. 3, 2014, in turn, to U.S. Provisional Application No. 61/443,161 filed Feb. 15, 2011, the entire contents of which are herein incorporated by reference. U.S. patent application Ser. No. 13/397,236 also claims the benefit of priority under 35 U.S.C. § 119 to European Patent Application No. 11154437.5 filed in Europe on Feb. 15, 2011, the entire contents of which are herein incorporated by reference.

FIELD

Disclosed is the use of renewable oil in a hydrotreatment process, for example, for the production of hydrocarbons. Also disclosed is the use of renewable oil comprising less than 1 ppm of iron, for the production of liquid fuel components or components which can be converted to liquid fuels.

BACKGROUND INFORMATION

Liquid fuel components are mainly based on crude oil. There is an ever growing demand for liquid fuels with lower $CO_2$ emissions compared to crude oil based fuels. Various renewable sources have been used as alternatives for crude oil fuels. Methods for converting biomass to liquid fuels include transesterifications of triglycerides to alkylester, hydrotreatment of oils and fats to paraffins, and renewable diesel obtained through gasification and the Fischer-Tropsh process. One of the most promising and furthest developed method is hydrogenation of vegetable oil (HVO) or animal fats to produce paraffins, which can further be refined, e.g., through isomerisation reactions to renewable diesel with excellent properties.

Vegetable oils and animal based fats can be processed to decompose the ester and/or fatty acid structure and to saturate the double bonds of the hydrocarbon backbone thus obtaining about 80-85% of n-paraffins relative to the mass of the starting material. This product can be directly used as a middle distillate fuel component. The cold flow properties of n-paraffins can be enhanced in an isomerisation step where iso-paraffins are formed. A method of producing iso-paraffins from vegetable oils and animal fats is presented in European Patent Document No. EP 1 396 531.

Certain impurities present in the renewable oil can be harmful for the performance of the hydrotreatment/deoxygenation catalyst. Triglycerides can be converted to hydrocarbons through a hydrodeoxygenation pathway using classical hydrodesulphurisation (HDS) catalyst such as NiMo and CoMo HDS catalysts. However, the catalyst has been shown to be deactivated as a result of phosphorous in the feedstock. In publication Kubicka et al (2010) it is shown that elimination of phosphorous from the feedstock is crucial to prevent rapid catalyst deactivation.

U.S. Patent Application Publication No. 2007/0010682 discloses a process for the production of diesel range hydrocarbons from bio oils and fats, which method includes hydrodeoxygenation and hydroisomerisation to achieve fuel components with excellent performance. It is also acknowledged that in order to avoid catalyst deactivation and undesired side reactions the amount of alkali metals and alkaline earth metals are less than 1 w-ppm calculated as elemental metal and phosphorus content less than 5 w-ppm. Degumming and bleaching are suggested to remove the impurities from the feed. In bleaching the refined oil feed is heated and mixed with natural or activated bleaching clay to remove impurities such as chlorophyll, phosphoric compounds and metals remaining in the oil after degumming.

There exist numerous commercial bleaching clays, which can be used in the bleaching of renewable oils. European Patent Document No. EP 0 507 217 discloses a porous base-treated inorganic adsorbent for removal of contaminants such as free fatty acids and metals from glyceride oils. The adsorbent is capable of reducing the levels of phosphorus to below 0.3 ppm and the level of metals to below 0.1 ppm.

In previous laboratory scale experiments it has been shown that triglycerides, e.g., in vegetable oils can be converted to hydrocarbons in hydrotreatment reactions. However, in large scale production of hydrotreated vegetable oil some difficulties have occurred over time. A significant increase in the pressure drop over the hydrodeoxygenation catalyst bed was observed. In normal running conditions there is a higher pressure at the top of the catalyst bed compared to the pressure at the bottom of the catalyst bed and this difference is called the pressure drop. The pressure drop drives the feed stream forward in the reactor. Over time, continuous plugging of the catalyst increases the pressure drop and could lead to complete plugging of the flow in the catalyst bed. An increase in the pressure drop was observed after some production time even if the feed contained only trace amounts of phosphorous and metal impurities such as Na, Ca and Mg.

These findings indicate that the hydrotreatment of glyceride oils from renewable sources still needs improvements and especially large scale production encounters problems which could not have been foreseen from the early laboratory scale experiments.

SUMMARY

According to an exemplary aspect, disclosed is a method for preparing a hydrocarbon, the method comprising: subjecting a bio oil from at least one renewable source to a hydrotreatment process, wherein in the hydrotreatment process, hydrocarbons are formed from said bio oil in a catalytic reaction employing a catalyst, wherein an iron content of said bio oil is less than 1 w-ppm calculated as elemental iron.

DETAILED DESCRIPTION

Disclosed is the use of bio oil from at least one renewable source, in a hydrotreatment process, in which process hydrocarbons are formed in a catalytic reaction and the iron content of the bio oil is less than 1 w-ppm, for example, less than 0.5 and, for example, less than 0.25 w-ppm calculated as elemental iron. The use of bio oil with extremely low content of iron can be employed to reduce or avoid plugging of the catalyst used in the hydrotreatment reaction.

An exemplary embodiment relates to the use of a glyceride oil from at least one renewable source in a hydrotreatment process, in which process hydrocarbons are formed in a catalytic reaction and the iron content of the glyceride oil is less than 1 w-ppm, for example, less than 0.5 w-ppm and, for example, 0.25 w-ppm calculated as elemental iron.

The hydrotreating catalyst was found to be plugged, for example, in large scale production over a certain time. The particles responsible for the plugging of the catalyst were found upon analysis to contain high amounts of phosphorous and metals. Further studies lead to the surprising finding that the iron content of the feed used in the hydrotreatment process is responsible for the plugging of the catalyst. An exemplary aspect therefore relates to renewable oil with very low iron content as the starting material for a hydrotreatment process.

Renewable oil enables longer running time of hydrotreating catalysts without plugging. Previous studies have established that impurities such as phosphorous and Na, Ca and Mg metals present in the feedstock may be responsible for deactivation of the catalyst. An exemplary aspect can address the problem of catalyst plugging and ensure smooth running of the process and stable reaction conditions allowing manufacture of hydrocarbons from glyceride oil with high conversion rate and high selectivity.

In addition, an exemplary aspect can prevent the hydrotreating catalyst from deactivation, or reduce the degree of deactivation, and the low amount of Fe in the oil minimises the oxidation of the renewable oil. Iron compounds can act as oxidants.

Here, bio oil is understood to mean any oil originating from a renewable (bio) source, including, for example, vegetable, animal or microbial sources. Bio oils can comprise at least fatty acids or fatty acid derivatives such as glycerides, alkyl esters of fatty acids, fatty acid alcohols or soaps.

Here, glyceride oil is understood to mean any oil which comprises triacylglycerides. The glyceride oil may also comprise di- and monoacylglycerides as well as fatty acids and their derivatives such as alkyl esters especially methyl esters. The chain length of the hydrocarbon chains in the glyceride oil can be from at least C8 up to C24. The term glyceride oil is meant to include at least, but not limited to rapeseed oil, colza oil canola oil, tall oil, sunflower oil, soybean oil, hempseed oil, cottonseed oil, corn oil, olive oil, linseed oil, mustard oil, palm oil, peanut oil, castor oil, coconut oil, camellia oil, jatropha oil, oils derived from microbial sources, which are possible genetically modified and includes at least algae, bacteria, moulds and filamentous fungi; animal fats, fish oil, lard, tallow, train oil, recycled fats from the food industry and any mixture of the oils.

Here, oil from renewable source or renewable oil is understood to mean any oil originating from a source that can be considered renewable, i.e., not fossil. Renewable sources include at least all plant (vegetable) and animal based sources, but also microbial based sources such as algae, bacteria, moulds and filamentous fungi etc. Re-use of spent oil from food industry is also considered a renewable source as well as oils obtained by conversion of wastes, such as municipal and slaughterhouse wastes.

Here the term hydrotreatment includes at least hydrodeoxygenation (HDO) and is understood as a collective term for all catalytic processes, which removes oxygen from organic oxygen compounds in the form of water, sulphur from organic sulphur compounds in the form of dihydrogen sulphide ($H_2S$), nitrogen from organic nitrogen compounds in the form of ammonia ($NH_3$) (hydrodenitrogenation, HDN) and halogens, for example chlorine from organic chloride compounds in the form of hydrochloric acid (HCl) (hydrodechlorination, HDCl), for example, under the influence of sulphided NiMo or sulphided CoMo catalysts. Hydrotreatment is here understood to include also decarboxylation/decarbonylation, i.e., removal of oxygen in the form of COx.

Hydroisomerisation or isomerisation is here understood to mean any process in which branches on the hydrocarbon backbone are formed and isoparaffins are produced. For example, methyl and ethyl side-chains are formed in the isomerisation step.

Disclosed is the use of bio oil, for example, glyceride oil, from at least one renewable source in a hydrotreatment process, in which process hydrocarbons are converted from the bio oil in a catalytic reaction and the iron content of the bio oil is less than 1 w-ppm, for example, less than 0.5 w-ppm, and, for example, less than 0.25 w-ppm, calculated as elemental iron. The hydrotreatment process is any catalytic process, such as a hydrodeoxygenation process performed using a trickle-bed reactor, in which, for example, glyceride oil material is treated with hydrogen to form hydrocarbons. Hydrodeoxygenation can be performed under a pressure from 10 to 150 bar, at a temperature of from 200 to 400° C. and using a hydrogenation catalyst containing metals from Group VIII and/or VIB of the Periodic System. For example, the hydrogenation catalysts are supported Pd, Pt, Ni, NiMo or CoMo catalyst, the support being alumina and/or silica. Exemplary catalysts are NiMo/Al2O3 and CoMo/Al2O3.

In order to improve the properties, especially the cold flow properties, of the formed hydrocarbons, the hydrotreatment step can be followed by an isomerisation step. In the isomerisation step the hydrocarbons undergo an isomerisation reaction whereby isoparaffins are formed.

A rapid increase in the pressure drop of the hydrotreatment reactor was noticed to occur in large scale production facilities. The reactor was opened and a substantial amount of dust-like particles was found inside the reactor. The dust-like particles were believed to be the cause of the plugging and increase in pressure drop over the catalyst bed. Analyses of dust-like particles revealed metals originating from feedstock (mainly Fe, Ca, Mg, Na) as well as phosphorus and carbon. Introducing less contaminated feedstock into the process has dramatically decreased the rate of pressure drop increase in the hydrotreating reactor. The plugging phenomenon was studied in more detail with a set of laboratory reactor experiments illustrated in the examples.

Based on the experiments with palm oil having very low level of impurities, a catalyst cycle length based on catalyst deactivation with pure feedstock can be calculated. Furthermore, based on plant operating experience the rate of reactor plugging can be correlated with iron content. From this information, it can be concluded that bio-based feedstock (glyceride oil) to be used as feed material for hydrotreatment reaction can be purified to iron content of less than 1 to 0.2 w-ppm (depending on the dimensioning design WHSV of the hydrodeoxygenation reactor and expected life cycle of the catalyst), for example, in order not to shorten the catalyst cycle length due to pressure drop increase. For efficient and profitable plant operation, the Fe content of the feedstock of the hydrogenation reactor can be less than 0.5 w-ppm, for example, less than 0.25 w-ppm (w-ppm refers here to ppm by weight). This purification result can be obtained (depending on used feedstock) using pre-treatment methods, such as degumming and bleaching, or alternatively new pre-treatment technologies or a combination thereof. Thus, disclosed is a glyceride oil intermediate, which intermediate consists of glyceride oil from at least one renewable source and the iron content of said glyceride oil is less than 1 w-ppm calculated as elemental iron, for example, less than 0.5 w-ppm and, for example, less than 0.25 w-ppm.

EXAMPLES

Undiluted glyceride oil was fed with high WHSV (8-10) through a bed consisting of hydrotreatment catalyst diluted in 1:2 ratio with quartz sand. Sand dilution was estimated to act as a filter, magnifying the plugging effect of the dust-like particles. This setup enabled reactor plugging to occur in days rather than months as in a reactor on an industrial scale plant. The reactor was considered to be plugged when a pressure drop of 3 bar was reached across the reactor, initial pressure being 0.5 bar.

First, a reference run (plant reference run) was conducted with degummed palm oil as the glyceride oil feed having rather high level of impurities (Experiment 1). Experiment 1 was repeated (Experiment 2). This test was repeated without any catalyst to demonstrate the effect of presence of catalyst in reactor plugging (Experiment 6). Experiments were then continued with bleached palm oil having very low levels of impurities (Experiment 3), filtered animal fat with high levels of P and Na but almost no other metals (Experiment 4), and finally bleached animal fat with moderate levels of P and Fe but almost no other metals (Experiment 5).

A summary of the conducted experiments is shown below:
Plant reference run with degummed palm oil (Experiment 1)
Repetition of experiment 1 with degummed palm oil (Experiment 2)
A run with bleached palm oil (Experiment 3)
A run with filtered animal fat (Experiment 4)
A run with bleached animal fat (Experiment 5)
A run with degummed palm oil repeated without catalyst (Experiment 6)

The composition of the dust-like particles was determined and the amount of the dust-like particles was measured after the experiment by separating the quartz sand and dust-like particles from the catalyst by screening and analysing the sand+dust mixture with wave length dispersive a X-ray fluorescence spectrometer (Bruker AXS S4 Explorer), with helium as measurement atmosphere.

The results of the analyses in the experiments are shown in following Table 1.

TABLE 1

Total increase in pressure drop, total cumulative feed through reactor; feed impurity levels, impurities found in catalyst, impurities found in sand + dust

| | Experiment No. | | | | | |
|---|---|---|---|---|---|---|
| | 1 | 2 | 3 | 4 | 5 | 6 |
| Initial dP/bar | 0.55 | 0.62 | 0.62 | 0.62 | 0.61 | 0.59 |
| Final dP/bar | 3.8 | 2.9 | 2.5 | 1.6 | 4.44 | 1.0 |
| delta(dP)/bar | 3.25 | 2.28 | 1.88 | 0.98 | 3.83 | 0.41 |

TABLE 1-continued

Total increase in pressure drop, total cumulative feed through reactor; feed impurity levels, impurities found in catalyst, impurities found in sand + dust

| | Experiment No. | | | | | |
|---|---|---|---|---|---|---|
| | 1 | 2 | 3 | 4 | 5 | 6 |
| Cumulative feed kg | 31.8 | 31.6 | 10.27 | 25.3 | 22.6 | 28.9 |
| Plugging rate mbar/kgfeed | 102.1 | 72.1 | 18.3 | 38.8 | 169.7 | 14.2 |
| Feed impurity concentrations | | | | | | |
| P/ppm | 3.8 | 3.7 | 0.6 | 24 | 5.7 | 3.8 |
| Ca/ppm | 1.2 | 1.1 | 0.3 | 0.6 | 0.1 | 1.2 |
| Fe/ppm | 1.2 | 1.3 | 0.6 | 0.1 | 1.8 | 1.2 |
| Na/ppm | 1 | 0 | 0 | 6 | 0 | 1 |
| Mg/ppm | 0.2 | 0 | 0 | 0.3 | 0.2 | 0.2 |
| Impurities found in sand + dust | | | | | | |
| P/mg | 425 | 309 | 154 | 154 | 309 | 301 |
| Ca/mg | 77 | 77 | 4 | 4 | 0 | 6 |
| Fe/mg | 116 | 116 | 77 | 54 | 174 | 18 |
| Na/mg | 77 | 39 | 0 | 54 | 0 | 6 |
| Mg/mg | 0 | 0 | 0 | 4 | 0 | 0 |
| Impurities found in catalyst | | | | | | |
| P/mg | 60 | 50 | 20 | 206 | 30 | |
| Ca/mg | 10 | 7 | 5 | 1 | 0 | |
| Fe/mg | 30 | 22.5 | 85 | 14 | 70 | |
| Na/mg | 10 | 12 | 5 | 13 | 0 | |
| Mg/mg | 0 | 0 | 0 | 0 | 0 | |

Figure 1:
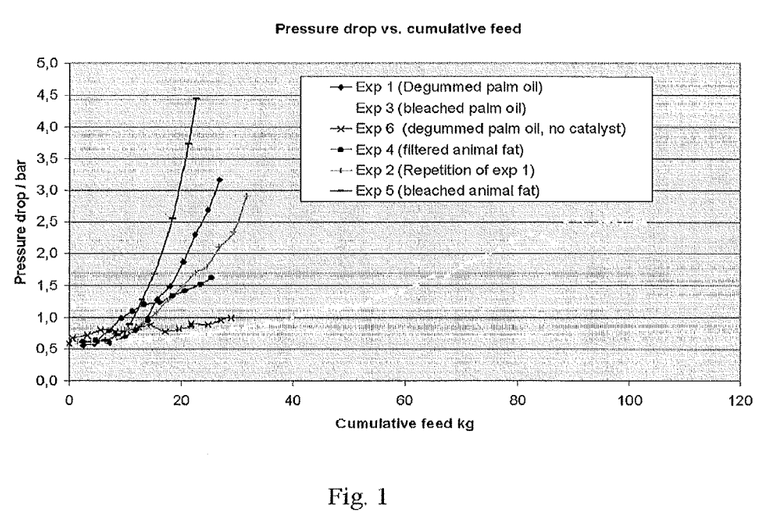
FIG. 1 shows the pressure drop over the catalyst bed in relation to the cumulative feed, in accordance with an exemplary aspect.

The pressure drop correlated with cumulative feed in each Experiment is presented in FIG. 1.

Figure 2:
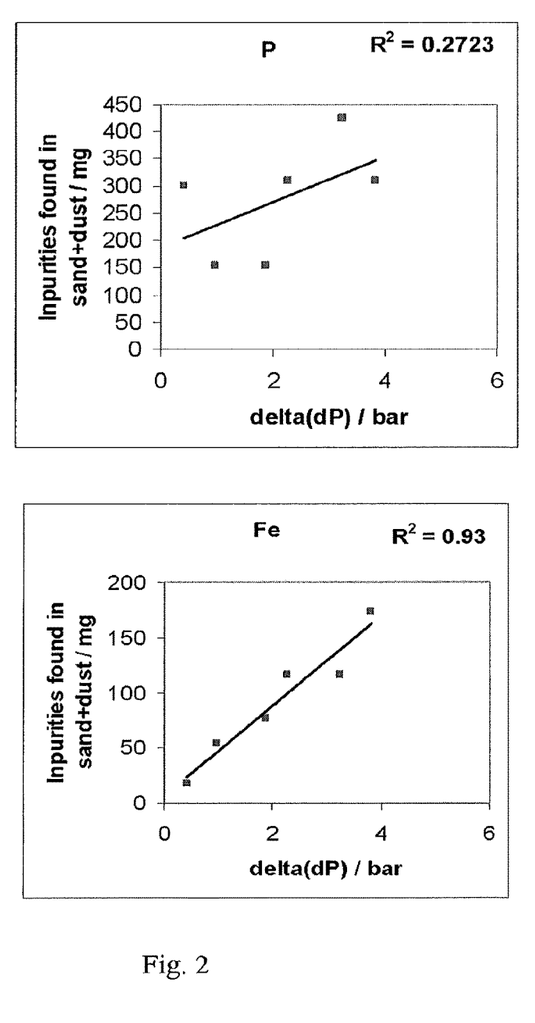
FIG. 2 shows the correlation between absolute increase in pressure drop and absolute masses of P and Fe found in the dust, in accordance with an exemplary aspect.

The absolute amounts of individual impurities in the dust-like particles were then correlated with the absolute pressure drop increases in corresponding experiment. Results are shown as correlation plots with R2-values for P and Fe in FIG. 2 and for all measured impurities in Table 2 below.

TABLE 2

Correlation between absolute increase in pressure drop and absolute masses of impurities found in dust

| Impurity | $R^2$ |
|---|---|
| P | 0.27 |
| Ca | 0.12 |
| Fe | 0.93 |
| Na | 0.01 |
| Mg | 0.18 |

Figure 3:
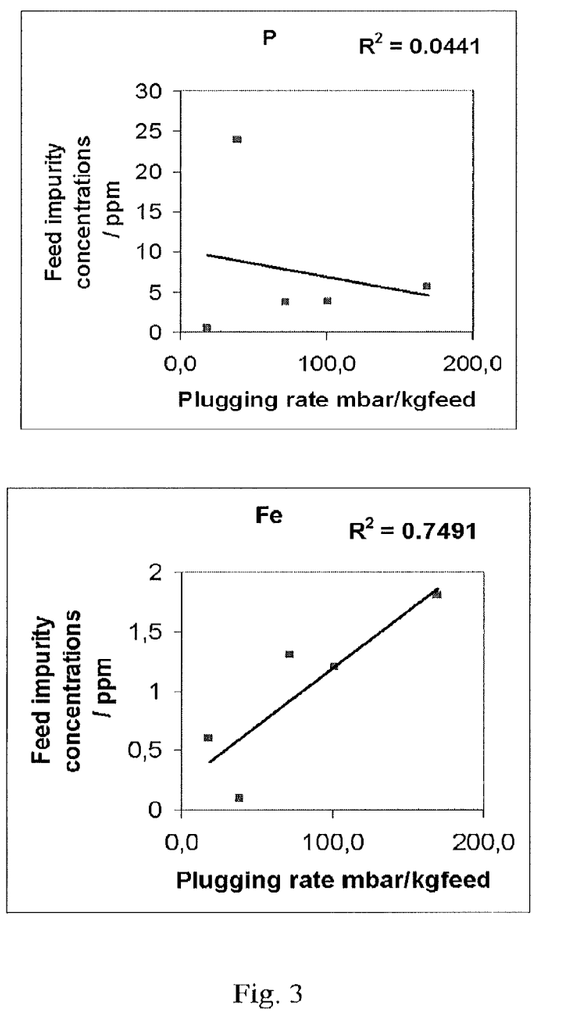
FIG. 3 shows the correlation between rate of increase in pressure drop (in bar/kg (feed) and concentrations of P and Fe in the feed, in accordance with an exemplary aspect.

A relative plugging rate can be calculated for each experiment by dividing the increase in pressure drop with total cumulative feed introduced in the reactor throughout the experiment. Correlating this plugging rate with impurities in corresponding feedstocks gives the plots shown in FIG. 3 for P and Fe. This correlation for all measured impurities is shown in table 3. The experiment without catalyst is excluded from FIG. 3, due to different rate of dust formation with and without catalyst.

TABLE 3

Correlation between rate of increase in pressure drop (in bar/kg(feed) and concentrations of impurities in feed.

| Impurity | $R^2$ |
|---|---|
| P | 0.04 |
| Ca | 0.02 |
| Fe | 0.75 |
| Na | 0.14 |
| Mg | 0.10 |

According to these results, iron is the only impurity in the dust correlating strongly with the increase in pressure drop over the catalyst bed.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A method for avoiding catalyst plugging that causes an increase in the pressure drop of the hydrotreatment reactor during hydrotreatment comprising: purifying a biological feedstock from at least one renewable source that has an iron content above 1 w-ppm calculated as elemental iron to an iron content from 0.25 to 0.5 w-ppm; hydrotreating the purified biological feedstock from at least one renewable source with a catalyst to form hydrocarbons during a catalytic reaction in a trickle bed reactor; and avoiding plugging of the catalyst used in hydrotreating that causes an increase in the pressure drop of the hydrotreatment reactor.

2. The method according to claim 1, wherein the biological feedstock is selected from the group consisting of rapeseed oil, colza oil, canola oil, tall oil, sunflower oil, soybean oil, hempseed oil, cottonseed oil, corn oil, olive oil, linseed oil, mustard oil, palm oil, peanut oil, castor oil, coconut oil, camellia oil, jatropha oil, an oil derived from a microbial source, animal fat, fish oil, lard, tallow, train oil, recycled fat from the food industry, and a mixture thereof.

3. The method according to claim 1, wherein the hydrocarbons formed in the hydrotreating are further processed in a hydroisomerisation process to iso-paraffins.

4. The method according to claim 2, wherein the microbial source is algae, bacteria, molds, filamentous fungi or a combination thereof.

5. The method according to claim 1, wherein the hydrodeoxygenation is performed under a pressure from 10 to 150 bar, and at a temperature of from 200 to 400° C.

6. The method according to claim 1, wherein the catalyst comprises Pd, Pt, Ni, NiMo or CoMo, and a support of alumina and/or silica.

7. The method according to claim 1, wherein the catalyst comprises a NiMo/$Al_2O_3$ catalyst, a CoMo/$Al_2O_3$ catalyst, or a combination thereof.

8. The method according to claim 3, wherein the iso-paraffins are converted into components for use in products selected from the group consisting of a base oil, lubrication oil, heating oil, diesel fuel, gasoline, liquefied petroleum gas. aviation fuel, solvent and biogas.

9. The method according to claim 6, wherein the catalyst comprises a NiMo/$Al_2O_3$ catalyst, a CoMo/$Al_2O_3$ catalyst, or a combination thereof.

10. The method according to claim 1, wherein the purified biological feedstock has a phosphorous content that is greater than 5 w-ppm calculated as elemental phosphorous.

11. A method for avoiding catalyst plugging that causes an increase in the pressure drop of the hydrotreatment reactor during hydrotreatment comprising: purifying a biological feedstock from at least one renewable source to lower the content of impurities that have a correlation between the rate of increase in the pressure drop measured as bar/kg of biological feedstock and the concentration of impurity measured in ppm that is 0.75 or greater to a value between 0.25 to 0.5 w-ppm; hydrotreating the purified biological feedstock from at least one renewable source with a catalyst to form hydrocarbons during a catalytic reaction in a trickle bed reactor; and avoiding plugging of the catalyst used in hydrotreating that causes an increase in the pressure drop of the hydrotreatment reactor.

12. The method according to claim 11, wherein the biological feedstock is purified to lower only the content of impurities that have a correlation between the rate of increase in the pressure drop measured as bar/kg of biological feedstock and the concentration of impurity measured in ppm that is 0.75 or greater.

13. The method according to claim 11, wherein the content of impurities that have a correlation between the rate of increase in the pressure drop measured as bar/kg of biological feedstock and the concentration of impurity measured in ppm that is 0.75 or greater in the biological feedstock is above 1 ppm before purification.

14. The method according to claim 11, or 13 wherein the impurities that have a correlation between the rate of increase in the pressure drop measured as bar/kg of biological feedstock and the concentration of impurity measured in ppm that is 0.75 or greater is iron.

15. The method according to claim 11, wherein the biological feedstock is selected from the group consisting of rapeseed oil, colza oil, canola oil, tall oil, sunflower oil, soybean oil, hempseed oil, cottonseed oil, corn oil, olive oil, linseed oil, mustard oil, palm oil, peanut oil, castor oil, coconut oil, camellia oil, jatropha oil, an oil derived from a microbial source, animal fat, fish oil, lard, tallow, train oil, recycled fat from the food industry, and a mixture thereof.

16. The method according to claim 11, wherein the hydrocarbons formed in the hydrotreating are further processed in a hydroisomerisation process to iso-paraffins.

17. The method according to claim 16, wherein the microbial source is algae, bacteria, molds, filamentous fungi or a combination thereof.

18. The method according to claim 11, wherein the hydrodeoxygenation is performed under a pressure from 10 to 150 bar, and at a temperature of from 200 to 400° C.

19. The method according to claim 11, wherein the catalyst comprises Pd, Pt, Ni, NiMo or CoMo, and a support of alumina and/or silica.

20. The method according to claim 11, wherein the catalyst comprises a NiMo/$Al_2O_3$ catalyst, a CoMo/$Al_2O_3$ catalyst, or a combination thereof.

21. The method according to claim 16, wherein the iso-paraffins are converted into components for use in products selected from the group consisting of a base oil, lubrication oil, heating oil, diesel fuel, gasoline, liquefied petroleum gas, aviation fuel, solvent and biogas.

22. The method according to claim 19, wherein the catalyst comprises a NiMo/$Al_2O_3$ catalyst, a CoMo/$Al_2O_3$ catalyst, or a combination thereof.

23. The method according to claim 11, wherein the purified biological feedstock has a phosphorous content that is greater than 5 w-ppm calculated as elemental phosphorous.

* * * * *

UNITED STATES PATENT AND TRADEMARK OFFICE
CERTIFICATE OF CORRECTION

PATENT NO. : 9,969,940 B2
APPLICATION NO. : 14/932566
DATED : May 15, 2018
INVENTOR(S) : Tuomas Ouni, Vainö Sippola and Petri Lindqvist It is certified that error appears in the above-identified patent and that said Letters Patent is hereby corrected as shown below:

In the Claims

Claim 1, Column 7, Line 27, "increase in the pressure drop of the hydrotreatment reactor" should read --increase in a pressure drop of a hydrotreatment reactor--.

Claim 5, Column 7, Lines 51-52, "the hydrodeoxygenation is performed" should read --the hydrotreating is hydrodeoxygenation performed--.

Claim 11, Column 8, Line 5, "increase in the pressure drop of the hydrotreatment reactor" should read --increase in a pressure drop of a hydrotreatment reactor--.

Claim 11, Column 8, Lines 7-8, "to lower the content" should read --to lower a content--.

Claim 11, Column 8, Lines 8-9, "between the rate" should read --between a rate--.

Claim 11, Column 8, Line 10, "and the concentration" should read --and a concentration--.

Claim 17, Column 8, Line 48, "according to claim 16" should read --according to claim 15--.

Claim 18, Column 8, Lines 51-52, "the hydrodeoxygenation is performed" should read --the hydrotreating is hydrodeoxygenation performed--.

Signed and Sealed this
Thirtieth Day of April, 2019

Andrei Iancu
*Director of the United States Patent and Trademark Office*